US012740823B2

(12) United States Patent
Gou et al.

(10) Patent No.: US 12,740,823 B2
(45) Date of Patent: Sep. 22, 2026

(54) RADIO FREQUENCY CATHETER CONTROLLING SYSTEM AND METHOD

(71) Applicant: Acotec Scientific Co., Ltd., Beijing (CN)

(72) Inventors: Huiyi Gou, Beijing (CN); Dawei Cao, Beijing (CN); Zhimin Chen, Beijing (CN)

(73) Assignee: Acotec Scientific Co., Ltd., Beijing (CN)

( * ) Notice: Subject to any disclaimer, the term of this patent is extended or adjusted under 35 U.S.C. 154(b) by 209 days.

(21) Appl. No.: 18/664,576

(22) Filed: May 15, 2024

(65) Prior Publication Data

US 2025/0017643 A1 Jan. 16, 2025

(30) Foreign Application Priority Data

Jul. 14, 2023 (CN) ........................ 202310862926.0

(51) Int. Cl.
*A61B 18/12* (2006.01)
*A61B 18/08* (2006.01)
(Continued)

(52) U.S. Cl.
CPC ........ *A61B 18/1206* (2013.01); *A61B 18/082* (2013.01); *A61B 18/1492* (2013.01);
(Continued)

(58) Field of Classification Search
CPC ... A61B 18/082; A61B 18/12; A61B 18/1206; A61B 18/14; A61B 18/1492;
(Continued)

(56) References Cited

U.S. PATENT DOCUMENTS 5,755,760 A * 5/1998 Maguire ........... A61M 25/0138 607/122
5,916,213 A 6/1999 Haissaguerre
(Continued)

FOREIGN PATENT DOCUMENTS

CN 205215353 U 5/2016
CN 111067617 A 4/2020
(Continued)

OTHER PUBLICATIONS

CNIPA, Office Action and Search Report in Chinese Application No. 202310862926, Aug. 18, 2023, 14 pages.
(Continued)

*Primary Examiner* — Michael F Peffley
(74) *Attorney, Agent, or Firm* — Acotec Scientific IP Legal

(57) ABSTRACT

The present disclosure provides an RF catheter controlling system and an RF catheter controlling method. The system includes: a logic control unit configured to receive a target command, and generate a control signal in accordance with the target command, the target command being used to indicate a target mode of an RF catheter, the control signal carrying information about at least one RF parameter corresponding to the target mode; and an RF generation module in communication with the logic control unit and configured to control the RF catheter to operate in the target mode in accordance with the information about the at least one RF parameter corresponding to the target mode.

8 Claims, 4 Drawing Sheets

(51) Int. Cl.
*A61B 18/14* (2006.01)
*A61B 18/00* (2006.01)

(52) U.S. Cl.
CPC ............... *A61B 2018/00345* (2013.01); *A61B 2018/00577* (2013.01); *A61B 2018/00708* (2013.01); *A61B 2018/00714* (2013.01); *A61B 2018/00732* (2013.01); *A61B 2018/00755* (2013.01); *A61B 2018/00761* (2013.01); *A61B 2018/124* (2013.01); *A61B 2018/1253* (2013.01); *A61B 2018/126* (2013.01)

(58) Field of Classification Search
CPC ........... A61B 2018/00345; A61B 2018/00577; A61B 2018/00702; A61B 2018/00708; A61B 2018/00714; A61B 2018/00732; A61B 2018/00755; A61B 2018/00761; A61B 2018/00791; A61B 2018/00875; A61B 2018/124; A61B 2018/1253; A61B 2018/126
See application file for complete search history.

(56) References Cited

U.S. PATENT DOCUMENTS 6,033,397 A 3/2000 Laufer
6,036,687 A 3/2000 Laufer
6,068,629 A 5/2000 Haissaguerre
6,071,277 A 6/2000 Farley
6,135,997 A 10/2000 Laufer
6,139,527 A 10/2000 Laufer
6,328,735 B1 * 12/2001 Curley .................. A61B 18/04 606/14
6,613,045 B1 9/2003 Laufer
7,625,372 B2 12/2009 Esch
7,702,397 B2 4/2010 Fredricks
7,955,369 B2 6/2011 Thompson
8,321,019 B2 11/2012 Esch
8,361,061 B2 1/2013 Esch
8,636,729 B2 1/2014 Esch
8,646,460 B2 2/2014 Utley
8,678,646 B2 3/2014 Klimovitch
8,702,697 B2 * 4/2014 Curley ................ A61B 18/082 606/41
8,715,276 B2 5/2014 Thompson
8,721,634 B2 5/2014 Esch
8,852,178 B2 10/2014 Thompson
9,113,929 B2 8/2015 Parsonage
9,289,258 B2 3/2016 Cohen
9,393,069 B2 7/2016 Stern
10,220,187 B2 3/2019 de la Rama
11,730,499 B1 8/2023 Thio
12,402,941 B2 9/2025 Laughner
12,414,816 B2 9/2025 Govari
2007/0060944 A1 3/2007 Boldenow
2010/0106150 A1 4/2010 Thompson
2010/0114085 A1 5/2010 Thompson
2010/0145327 A1 6/2010 Thompson
2010/0286684 A1 * 11/2010 Hata ................. A61B 18/1492 606/41
2011/0034922 A1 2/2011 Thompson
2011/0046617 A1 2/2011 Thompson
2011/0054456 A1 3/2011 Thompson
2011/0230859 A1 9/2011 Galdonik
2011/0257645 A1 10/2011 Thompson
2012/0016344 A1 1/2012 Kusakabe
2012/0065636 A1 3/2012 Thompson
2012/0071873 A1 3/2012 Thompson
2012/0253313 A1 10/2012 Galdonik
2014/0012245 A1 1/2014 Esch
2014/0171941 A1 6/2014 Thompson
2014/0378970 A1 12/2014 Thompson
2015/0257774 A1 9/2015 Galdonik
2015/0272654 A1 10/2015 Esch
2016/0120598 A1 5/2016 Brink
2016/0166265 A1 6/2016 Nita
2016/0166266 A1 6/2016 Nita
2016/0354145 A1 12/2016 Stern
2017/0143947 A1 5/2017 Coulson
2017/0238951 A1 8/2017 Yang
2017/0239440 A1 8/2017 Yang
2017/0252536 A1 9/2017 Yang
2018/0093068 A1 4/2018 Nagao
2018/0242989 A1 8/2018 Nita
2018/0263642 A1 9/2018 Nita
2018/0303498 A1 10/2018 Galdonik
2018/0353194 A1 12/2018 Shaffer
2019/0142452 A1 5/2019 Trosper
2019/0231422 A1 8/2019 Stern
2019/0336727 A1 11/2019 Yang
2020/0001046 A1 1/2020 Yang
2020/0155181 A1 5/2020 Yang
2020/0170666 A1 6/2020 Trosper
2020/0179032 A1 6/2020 Esch
2020/0281649 A1 9/2020 Brink
2020/0297972 A1 9/2020 Yee
2020/0345404 A1 11/2020 Thompson
2020/0367917 A1 11/2020 Teigen
2020/0383698 A1 12/2020 Miao
2020/0397957 A1 12/2020 Teigen
2021/0128182 A1 5/2021 Teigen
2021/0128221 A1 * 5/2021 Neal, II ................. A61B 18/12
2021/0315598 A1 10/2021 Buck
2021/0330370 A1 * 10/2021 Macaraeg ............ A61B 18/082
2021/0353323 A1 11/2021 Teigen
2021/0361314 A1 11/2021 Teigen
2021/0369325 A1 * 12/2021 Callas .................... A61B 18/14
2021/0378696 A1 12/2021 Yang
2021/0393311 A1 12/2021 Przygoda
2022/0211975 A1 7/2022 Yang
2022/0280171 A1 9/2022 Teigen
2022/0323147 A1 10/2022 Hata
2023/0026412 A1 1/2023 Teigen
2023/0116973 A1 4/2023 Yang
2023/0270485 A1 8/2023 Thompson
2023/0380897 A1 11/2023 Liu
2024/0000469 A1 1/2024 Teigen
2024/0148427 A1 5/2024 Przygoda
2024/0350170 A1 10/2024 Koon
2025/0000565 A1 1/2025 Przygoda
2025/0072947 A1 3/2025 Zhao

FOREIGN PATENT DOCUMENTS

CN 111772784 A 10/2020
CN 115590602 A 1/2023
WO 2024250416 12/2024

OTHER PUBLICATIONS

CNIPA, Office Action and Search Report in Chinese Application No. 202310862926, Sep. 18, 2023, 15 pages.
CNIPA, Office Action and Search Report in Chinese Application No. 202310862926, Sep. 30, 2023, 17 pages.

* cited by examiner

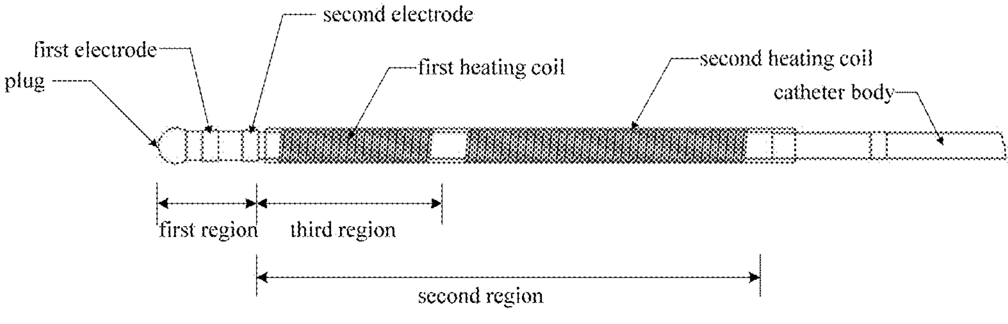
Fig. 6
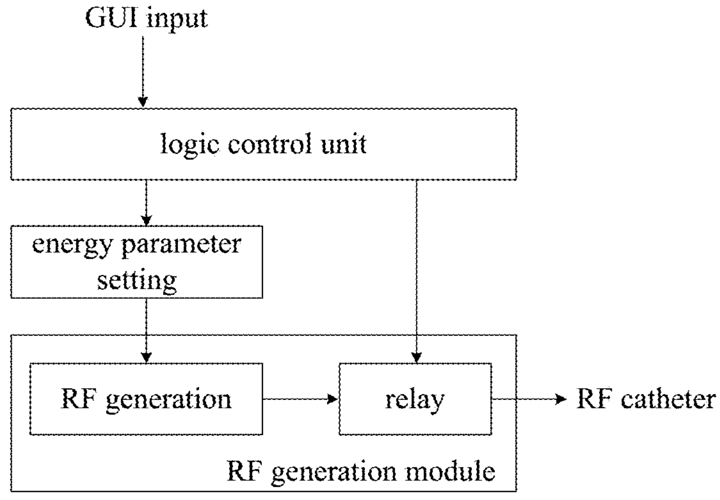
Fig. 7
handle PCBA
relay control
pad at proximal end
pad at distal end
RF+
RF_positive1
RF_output+
RF_positive2
second heating coil
RF_positive3
first heating coil
RF_output-
RF_negative
RF-
Fig. 8

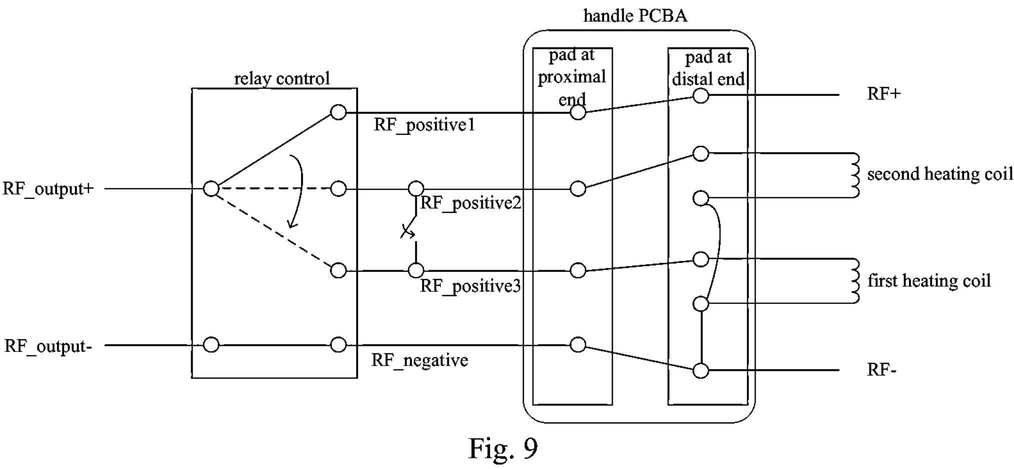

Fig. 9

101: receiving a target command, the target command being used to indicate a target mode of an RF catheter 102: generating a control signal in accordance with the target command, the control signal carrying information about at least one RF parameter corresponding to the target mode 103: controlling the RF catheter to operate in the target mode in accordance with the information about the at least one RF parameter

Fig. 10

RADIO FREQUENCY CATHETER CONTROLLING SYSTEM AND METHOD

TECHNICAL FIELD

The present disclosure relates to the field of Radio Frequency (RF) technology, in particular to an RF catheter controlling system and an RF catheter controlling method.

BACKGROUND

In the related art, there exist the following problems in an RF closure device for the treatment of varicose veins of a lower limb.

1. It is impossible for a single RF catheter to complete the RF closure on a superficial vein and a perforating vein of the lower limb simultaneously. During the surgery, different instruments need to be used, leading to a risk during the change of the instruments. In addition, an operation time is prolonged, and an economical burden of a patient increases.

2. The RF catheter is provided with a single heating coil. When the heating coil is long, the ablation efficiency is high, but it is impossible to perform the treatment on a short vein, a small saphenous vein, an accessory saphenous vein, and a branch/perforating branch. When the heating coil is short, it is able to perform the treatment on the short vein, but the ablation efficiency is low, and the operation time is prolonged significantly.

SUMMARY

An object of the present disclosure is to provide an RF catheter controlling system and an RF catheter controlling method, so as to complete the RF closure on the superficial vein and the perforating vein of the lower limb simultaneously while ensuring the ablation efficiency of an RF catheter.

In order to solve the above-mentioned problem, the present disclosure provides the following technical solutions.

In one aspect, the present disclosure provides in some embodiments an RF catheter controlling system, including: a logic control unit configured to receive a target command, and generate a control signal in accordance with the target command, the target command being used to indicate a target mode of the RF catheter, the control signal carrying information about at least one RF parameter corresponding to the target mode; and an RF generation module in communication with the logic control unit and configured to control the RF catheter to operate in the target mode in accordance with the information about the at least one RF parameter corresponding to the target mode.

In a possible embodiment of the present disclosure, the system further includes an upper computer and/or a peripheral interface in communication with the logic control unit, the logic control unit receives the target command from the upper computer and/or the peripheral interface, and the target command is generated when a button on an operation interface of the upper computer is pressed and/or inputted through a physical switch coupled to the peripheral interface.

In a possible embodiment of the present disclosure, the RF generation module is further configured to receive an RF start command or an RF stop command, and start an output of an RF signal in accordance with the RF start command in the target mode, or stop the output of the RF signal in accordance with the RF stop command in the target mode.

In a possible embodiment of the present disclosure, the target mode is one of a first mode, a second mode and a third mode; in the first mode, a first region of an RF energy output segment of the RF catheter operates, and the first region includes a first electrode and a second electrode spaced apart from each other; in the second mode, a second region of the RF energy output segment of the RF catheter operates, and the second region includes a first heating coil and a second heating coil spaced apart from each other; in the third mode, a third region of the RF energy output segment of the RF catheter operates, and the third region includes the first heating coil; and the first heating coil is arranged adjacent to the second electrode.

In a possible embodiment of the present disclosure, the RF generation module is configured to: in the first mode, generate a target RF signal in accordance with a first control signal, the first control signal carrying a first frequency parameter, a first power parameter, a first temperature parameter, a first load parameter, a first impedance parameter, a first output power parameter and a first treatment time parameter; in the second mode, generate the target RF signal in accordance with a second control signal, the second control signal carrying a second frequency parameter, a second power parameter, a second temperature parameter, a second load parameter, a second impedance parameter, a second output power parameter and a second treatment time parameter; and in the third mode, generate the RF frequency signal in accordance with a third control signal, the third control signal carrying a third frequency parameter, a third power parameter, a third temperature parameter, a third load parameter, a third impedance parameter, a third output power parameter and a third treatment time parameter. The first load parameter is a human tissue, the second load parameter is the first heating coil and the second heating coil, and the third load parameter is the first heating coil.

In a possible embodiment of the present disclosure, the RF generation module further includes: an RF signal generation unit configured to generate an RF signal; an RF positive pole configured to transmit the RF signal; an RF negative pole configured to receive an RF signal from an energy applying end of the RF catheter; and a switch circuit coupled to the RF positive pole, and configured to be electrically coupled to the first region of the RF catheter in the first mode to form a first loop, electrically coupled to the second region of the RF catheter in the second mode to form a second loop, and electrically coupled to the third region of the RF catheter in the third mode to form a third loop.

In a possible embodiment of the present disclosure, the switch circuit includes a first switch circuit, a first selection end of which is electrically coupled to the first region of the RF catheter to form the first loop, a second selection end of which is electrically coupled to the second region of the RF catheter to form the second loop, and a third selection end of which is electrically coupled to the third region of the RF catheter to form the third loop.

In a possible embodiment of the present disclosure, the switch circuit includes a second switch circuit, the second switch circuit includes a first-stage switch circuit and a second-stage switch circuit, a first selection end of the first-stage switch circuit is electrically coupled to the first region of the RF catheter to form the first loop, a second selection end of the first-stage switch circuit is electrically coupled to a first selection end of the second-stage switch circuit and the second region of the RF catheter to form the second loop, and a third selection end of the first-stage switch circuit is electrically coupled to a second selection end of the second-stage switch circuit and the third region of the RF catheter to form the third loop.

In another aspect, the present disclosure provides in some embodiments an RF catheter controlling method, including: receiving a target command, the target command being used to indicate a target mode of an RF catheter; generating a control signal in accordance with the target command, the control signal carrying information about at least one RF parameter corresponding to the target mode; and controlling the RF catheter to operate in the target mode in accordance with the information about the at least one RF parameter.

In a possible embodiment of the present disclosure, the method further includes: receiving an RF start command or an RF stop command; and starting an output of an RF signal in accordance with the RF start command in the target mode or stopping the output of the RF signal in accordance with the RF stop command in the target mode.

The present disclosure at least has the following beneficial effects.

According to the embodiments of the present disclosure, the logic control unit receives the target command and generates the control signal in accordance with the target command, the target command is used to indicate the target mode of the RF catheter, and the control signal carries the information about the at least one RF parameter corresponding to the target mode. The RF generation module is in communication with the logic control unit and configured to control the RF catheter to operate in the target mode in accordance with the information about the at least one RF parameter corresponding to the target mode. As a result, it is able to complete the RF closure on the superficial vein and the perforating vein of the lower limb simultaneously while ensuring the ablation efficiency of the RF catheter.

BRIEF DESCRIPTION OF THE DRAWINGS

FIG. 6 is a schematic view showing an energy output end at a catheter tip of the RF catheter controlling system according to one embodiment of the present disclosure;

FIG. 7 is a schematic view showing a single control for the RF catheter controlling system according to one embodiment of the present disclosure;

FIG. 8 is a circuit diagram of the RF catheter controlling system when heating coils are connected in series with each other according to one embodiment of the present disclosure;

FIG. 9 is a circuit diagram of the RF catheter controlling system when the heating coils are connected in parallel with each other according to one embodiment of the present disclosure; and FIG. 10 is a flow chart of an RF catheter controlling method according to one embodiment of the present disclosure.

DETAILED DESCRIPTION

The present disclosure will be described hereinafter in conjunction with the drawings and embodiments. The following embodiments are for illustrative purposes only, but shall not be used to limit the scope of the present disclosure. Actually, the embodiments are provided so as to facilitate the understanding of the scope of the present disclosure.

Figure 1:
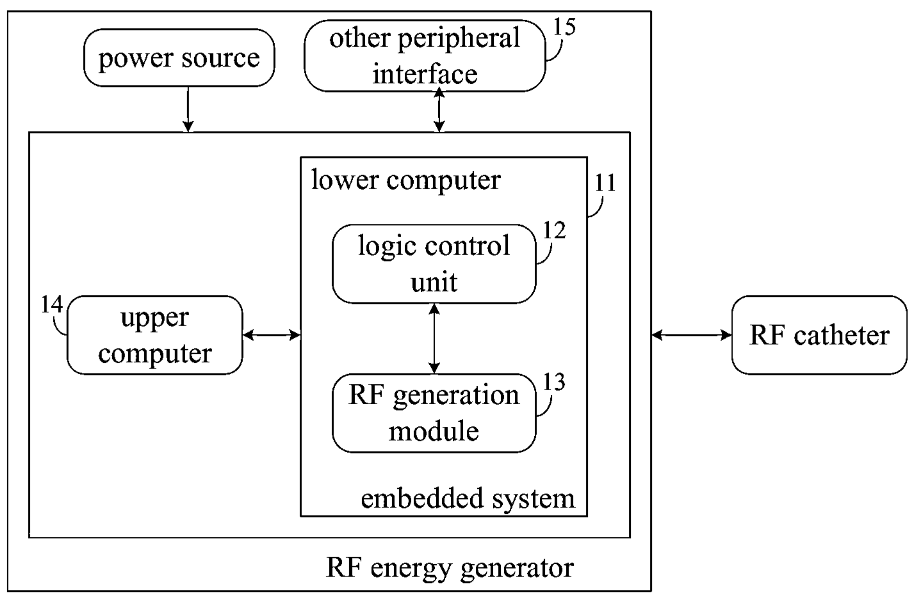
FIG. 1 is a schematic view showing an RF catheter controlling system according to one embodiment of the present disclosure.

As shown in FIG. 1, the present disclosure provides in some embodiments an RF catheter controlling system, which includes: a logic control unit 12 configured to receive a target command, and generate a control signal in accordance with the target command, the target command being used to indicate a target mode of the RF catheter, the control signal carrying information about at least one RF parameter corresponding to the target mode; and an RF generation module 13 in communication with the logic control unit 12 and configured to control the RF catheter to operate in the target mode in accordance with the information about the at least one RF parameter corresponding to the target mode.

According to the embodiments of the present disclosure, the logic control unit receives the target command and generates the control signal in accordance with the target command, the target command is used to indicate the target mode of the RF catheter, and the control signal carries the information about the at least one RF parameter corresponding to the target mode. The RF generation module is in communication with the logic control unit and configured to control the RF catheter to operate in the target mode in accordance with the information about the at least one RF parameter corresponding to the target mode. As a result, it is able to complete the RF closure on the superficial vein and the perforating vein of the lower limb simultaneously while ensuring the ablation efficiency of the RF catheter.

Figure 2:
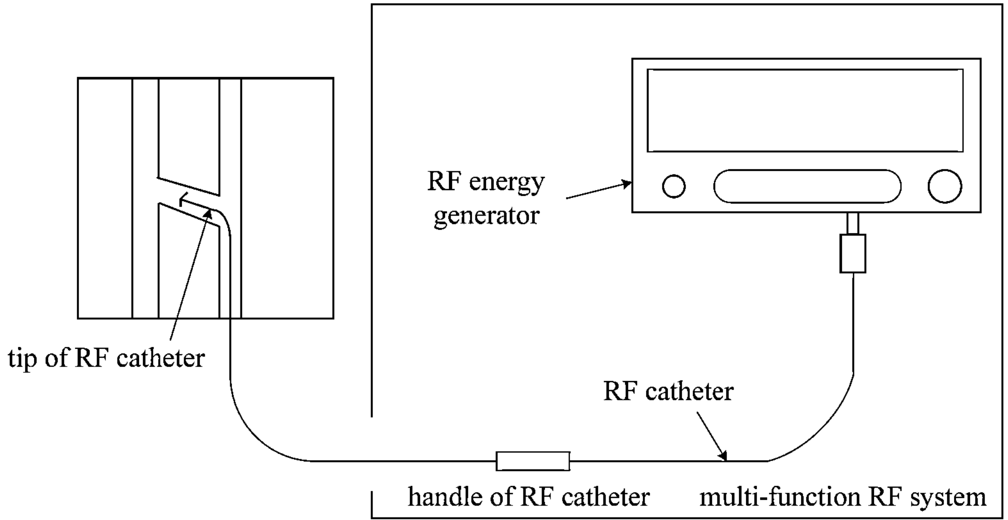
FIG. 2 is a schematic view showing a working principle of the RF catheter controlling system according to one embodiment of the present disclosure.

As shown in FIG. 2, the system includes an RF energy generator, an RF catheter integrated cable, and an integrated circuit in a handle of the RF catheter. The RF energy generator includes an upper computer 14, a lower computer 11, a power source and other peripherals.

The lower computer 11 includes the logic control unit 12 and the RF generation module 13. The logic control unit 12 receives the target command from the upper computer 14 or a peripheral interface 15, transmits the control signal to the RF generation module 13 in accordance with the target command, and control a logic switch in the RF generation module 13 to be at a target position. The RF generation module 13 generates an RF in accordance with parameter information carried in the control signal, and the RF is transmitted through a target circuit in which the logic switch is at the target position to an energy applying end of a catheter tip, so as to achieve a predetermined therapeutic effect in the target mode.

Figure 3:
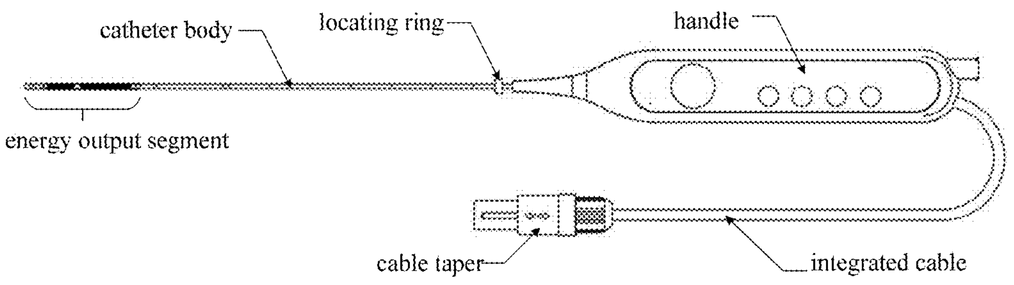
FIG. 3 is a schematic view showing an RF catheter for the RF catheter controlling system according to one embodiment of the present disclosure.

As shown in FIG. 3, the RF catheter includes a catheter body, an energy output segment at one end of the catheter body, and a locating ring, a handle, an integrated cable and a cable taper arranged on the catheter body.

The energy output segment includes one or two annular electrodes, and a plurality of heating coils arranged in an axial direction. Through RF heating, energy is supplied to a blood vessel at a position where a lesion occurs.

The catheter body is of a tubular structure with an outer diameter of 1 mm to 2.5 mm. The catheter body is provided with marking tapes at different lengths and in different colors, so as to indicate a distance for which the catheter needs to move back after the treatment on a segment of the blood vessel. A plurality of cables and thermocouple lines is arranged in the catheter body, so as to transmit an RF current and a temperature signal. The catheter body is made of a medical-grade polymer, such as polyether-ether-ketone (PEEK), polyurethane (PU) or polyether block amide (PEBAX), and the marking tape is formed using a medical-grade ink or a medical-grade polymer film.

The locating ring is of an annular structure capable of sliding along the catheter body, so as to indicate a position of the catheter during the treatment, thereby to prevent the catheter from moving back too long or too short after the treatment on a segment of the blood vessel. The locating ring is made of a medical-grade polymer, e.g., PEEK, TPU or PE.

The handle includes a switch and a plurality of indicators. The switch is configured to dynamically select operating states of each heating element, and turn on or off the application of the RF energy. The indicator is configured to indicate a current operating state of the catheter, so as to facilitate the operation of a doctor and prevent the catheter from being used inaccurately.

The integrated cable includes a plurality of RF energy transmission lines and thermocouple compensation lines, and it is enclosed by an insulation layer. The integrated cable is configured to transmit the RF current, the temperature signal, and a switch triggering signal or a gear position adjustment signal.

The cable taper is coupled to an interface of the RF energy generator, so that the RF energy is supplied by the RF energy generator to the catheter tip, and the real-time temperature of the catheter tip is transmitted to the RF energy generator. In this way, it is able to control the magnitude of the outputted RF energy, thereby to maintain the energy application segment of the catheter at a certain temperature.

When the system in the embodiments of the present disclosure is used together with the above-mentioned RF catheter, it is able to complete the RF closure on the superficial vein and the perforating vein of the lower limb simultaneously while ensuring the ablation efficiency of the RF catheter. The energy output segment of the catheter tip is provided with a single electrode of two electrodes for the RF treatment on the perforating vein. In addition, the energy output segment of the catheter is provided with a plurality of heating coils arranged along an axial direction for the treatment on the superficial vein. Each heating coil is controlled independently and outputs the energy independently, and an operating mode of the RF catheter is selected dynamically in use. Through the plurality of heating coils, it is able to perform the ablation on a long vein segment and a short vein segment through a single catheter, without any attenuated ablation efficiency.

In a possible embodiment of the present disclosure, the system further includes an upper computer 14 and/or a peripheral interface 15 in communication with the logic control unit 12, the logic control unit 12 receives the target command from the upper computer 14 and/or the peripheral interface 15, and the target command is generated when a button on an operation interface of the upper computer is pressed and/or inputted through a physical switch coupled to the peripheral interface 15.

Figure 4:
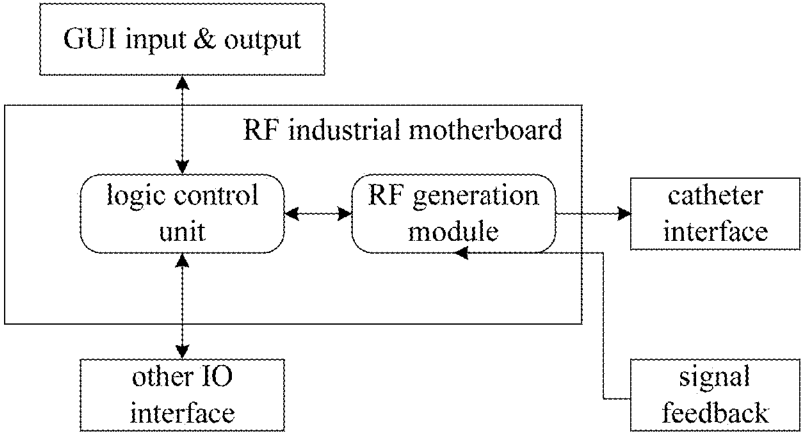
FIG. 4 is a schematic view showing a logic control for the RF catheter controlling system according to one embodiment of the present disclosure.
Figure 5:
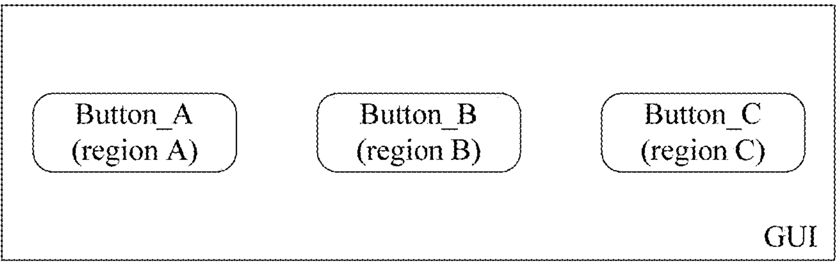
FIG. 5 is a schematic view showing a Graphical User Interface (GUI) of an upper computer of the RF catheter controlling system according to one embodiment of the present disclosure.

As shown in FIGS. 4 and 5, in the embodiments of the present disclosure, the target command is inputted into the logic control unit 12 through a button on a GUI of the upper computer.

Alternatively, the target command is further inputted through a peripheral unit coupled to the peripheral interface 15. The peripheral unit is a foot switch, a handle switch, a state indicator, a standby button, or a Universal Serial Bus (USB) interface. Of course, depending on the specific operating mode and requirement, the target command is also transmitted to the logic control unit 12 under the control of the upper computer 14 and the peripheral interface 15.

In a possible embodiment of the present disclosure, the RF generation module 13 is further configured to receive an RF start command or an RF stop command, and start an output of an RF signal in accordance with the RF start command in the target mode, or stop the output of the RF signal in accordance with the RF stop command in the target mode.

In the embodiments of the present disclosure, after the target mode is selected through the upper computer 14 or the peripheral interface 15, it is further necessary to transmit the RF start command to enable the RF generation module 13 to generate the target RF. Depending on the actual operating requirement, an on state and an off state of the RF generation module 13 are controlled through the GUI of the upper computer, or the other peripheral unit coupled to the peripheral interface 15, or both. For example, when the power source is on, the first mode is selected by default, and at this time, an RF start button on the GUI of the upper computer is selected so as to generate the RF energy. Alternatively, when the second mode or the third mode needs to be selected, a button on the GUI of the upper computer is selected, and the RF start command is transmitted through the other peripheral unit, e.g., the foot switch, so as to generate the RF energy. When the generation of the RF energy is controlled individually through the other peripheral unit, the peripheral interface 15 is arranged on the handle, and it may be a self-holding switching or a self-reset switch. When the generation of the RF energy is controlled through the buttons on the GUI, in order to prevent the occurrence of misoperation, the button may be pressed for several seconds so as to start the generation of the RF energy. When the generation of the RF energy needs to be stopped, it is unnecessary to long-press the button.

In the embodiments of the present disclosure, when the RF energy is outputted by the RF generation module 13, the RF stop command is transmitted by the logic control unit 12 in the following three circumstances: (1) an energy output duration reaches an upper limit; (2) an energy output stop command has been received from the GUI or the other peripheral interface 15; and (3) the communication between the logic control unit 12 and the RF generation module 13 or the other module is interrupted, or an RF energy output mechanism of the RF generation module 13 is unexpected.

In a possible embodiment of the present disclosure, the target mode is one of a first mode, a second mode and a third mode. In the first mode, a first region of an RF energy output segment of the RF catheter operates, and the first region includes a first electrode and a second electrode spaced apart from each other. In the second mode, a second region of the RF energy output segment of the RF catheter operates, and the second region includes a first heating coil and a second heating coil spaced apart from each other. In the third mode, a third region of the RF energy output segment of the RF catheter operates, and the third region includes the first heating coil. The first heating coil is arranged adjacent to the second electrode.

As shown in FIG. 6, in the embodiments of the present disclosure, the energy output segment of the catheter tip is divided into three regions which output the energy not at the same time and which are independent of each other. A region at a distal end of the catheter where the single or double annular electrodes are located is defined as the first region, and it has a smallest area when the energy is outputted in a target blood vessel. A region where the plurality of heating coils operate simultaneously is defined as the second region, and it has a largest area when the energy is outputted in the target blood vessel. A region where a single heating coil adjacent to the single or double annular electrodes operates is defined as the third region, and it has an area smaller than the second region and greater than the first region.

In the case that the RF generation module is in the first mode, the first electrode and the second electrode in the first region are each in an operating state, and the RF current is transmitted from the first electrode through the human tissue to the second electrode. A closed loop is formed through the catheter tip and the human tissue, and at this time, the RF energy is directly applied to the human tissue to generate a heat effect.

In the case that the RF generation module is in the second mode, the first heating coil and the second heating coil in the second region are each in an operating state. The RF current flows through the first heating coil and the second heating coil sequentially, and heat is generated due to the high resistivity of the heating coils. At this time, the energy is applied to an inner wall of a blood vessel through heat conduction, so as to achieve the ablation.

In the case that the RF generation module is in the third mode, the RF current flows through the first heating coil and back to the RF generation module. At this time, merely the first heating coil of the catheter tip takes effect, and the energy is applied to the inner wall of the blood vessel through heat conduction.

In the embodiments of the present disclosure, a plug is further provided in the first region and at a distal end of the catheter. In an interventional operation, the plug is in direct contact with the inner wall of the blood vessel at first, so the plug is provided with a smooth surface, so as to prevent any damage to the inner wall of the blood vessel. In addition, through the plug, it is able to prevent a body fluid from entering the catheter, thereby to prevent the occurrence of short circuit. The plug is made of a photosensitive adhesive or thermoplastic polyurethane (TPU).

Each of the first electrode and the second electrode is of a ring shape, and made of a platinum-iridium alloy or stainless steel. The two electrodes are insulated from each other. An RF signal cable is coupled to an inner wall of each electrode, and a thermocouple is arranged on the inner wall of the first or second electrode for temperature measurement. During the operation, the first electrode and the second electrode are of different polarities, and the RF current flows from one electrode through a human body to the other electrode, so as to generate heat and apply the heat onto the inner wall of the blood vessel. Each of the electrodes has an outer diameter of 1 mm to 2.5 mm and a length of 0.5 mm to 2 mm, and the two electrodes are spaced apart from each other by 0.2 mm to 2 mm.

Each of the first heating coil and the second heating coil is obtained through winding a high-resistivity metallic wire with an insulation layer. In order to reduce an inductance of the coil itself, a single metallic wire is folded and then wound in biflar manner. The metallic wire is made of a copper-nickel alloy, a nickel-chromium alloy, a nickel-chromium-iron alloy or an iron-chromium-aluminium alloy. The insulation layer is made of high density polyethylene (HDPE), polytetrafluoroethylene (PTFE) or polyimide (PI). The metallic wire has a diameter of 0.05 mm to 0.2 mm. The coils are spaced apart from each other by 0.5 mm to 10 mm, so as to facilitate the identification of different coils under an ultrasonic wave. Each heating coil is controlled independently and outputs the energy independently, and the heating coil is selected dynamically in use. When a current passes through the heating coil, a high temperature occurs due to high resistivity, and the heat is transferred to the inner wall of the blood vessel for ablation. Through the plurality of heating coils, it is able to perform the ablation on a long vein segment and a short vein segment through a single catheter, without any attenuated ablation efficiency.

Each of the first heating coil and the second heating coil is provided with a thermocouple, so as to measure a real-time temperature of the coil, and transmit a temperature signal to the RF generation module 13 in real time during the treatment when the energy applying end of the catheter tip is in the target mode. Under the effect of the temperature signal and the control signal from the logic control unit 12, the RF generation module 13 generates the target RF, so as to help the logic control unit 12 to control the output of the RF energy.

Each of the first heating coil and the second heating coil is further enclosed by a thermally-shrinkable tube which is made of fluoroplastics, e.g., fluorinated ethylene propylene (FEP) or PTFE. The thermally-shrinkable tube has a thickness of 0.05 mm to 0.5 mm, and it is sealed with an UV-curable adhesive at both ends. During the operation of the RF catheter, the thermally-shrinkable tube is used to prevent the RF catheter from be adhered to a human tissue, and insulate the coil from the human tissue.

In a possible embodiment of the present disclosure, the RF generation module 13 is configured to: in the first mode, generate a target RF signal in accordance with a first control signal, the first control signal carrying a first frequency parameter, a first power parameter, a first temperature parameter, a first load parameter, a first impedance parameter, a first output power parameter and a first treatment time parameter; in the second mode, generate the target RF signal in accordance with a second control signal, the second control signal carrying a second frequency parameter, a second power parameter, a second temperature parameter, a second load parameter, a second impedance parameter, a second output power parameter and a second treatment time parameter; and in the third mode, generate the RF frequency signal in accordance with a third control signal, the third control signal carrying a third frequency parameter, a third power parameter, a third temperature parameter, a third load parameter, a third impedance parameter, a third output power parameter and a third treatment time parameter. The first load parameter is a human tissue, the second load parameter is the first heating coil and the second heating coil, and the third load parameter is the first heating coil.

In the embodiments of the present disclosure, due to different energy applying mechanisms of the catheter tip, the RF generation module 13 has different energy generation mechanisms or parameters, as shown in Table 1.

TABLE 1

| parameters in different modes | | | |
|---|---|---|---|
| Mechanism/parameter | First mode | Second mode | Third mode |
| operating frequency | frequency $A_1$kHz | frequency $B_1$kHz | frequency $C_1$kHz |
| power control | constant temperature or power | constant temperature or power | constant temperature or power |

TABLE 1-continued parameters in different modes

| Mechanism/parameter | First mode | Second mode | Third mode |
|---|---|---|---|
| target temperature | $A_2$° C. | $B_2$° C. | $C_2$° C. |
| load | human tissue | heating coils B + C | heating coil C |
| impedance | $A_{31}$~$A_{32}$/Ω | $B_{31}$~$B_{32}$/Ω | $C_{31}$~$C_{32}$/Ω |
| output power | $A_4$w | $B_4$w | $C_4$w |
| treatment time | unlimited | $B_5$s/cycle | $C_5$s/cycle |

In the case that the RF generation module operates in different modes, the parameters of the target RF generated by the RF generation module 13, e.g., the operating frequency, the power mode, the target temperature, the load, the impedance, the output power and the treatment time in Table 1, are different.

In a possible embodiment of the present disclosure, the RF generation module 13 further includes: an RF signal generation unit configured to generate an RF signal; an RF positive pole configured to transmit the RF signal; an RF negative pole (RF_negative) configured to receive an RF signal from an energy applying end of the RF catheter; and a switch circuit coupled to the RF positive pole, and configured to be electrically coupled to the first region of the RF catheter in the first mode to form a first loop, electrically coupled to the second region of the RF catheter in the second mode to form a second loop, and electrically coupled to the third region of the RF catheter in the third mode to form a third loop.

As shown in FIG. 7, in the embodiments of the present disclosure, the RF generation module 13 is further provided with a logic switch, e.g., a relay, a switch element and a master controller. When the operating mode is selected by an operator through the GUI of the upper computer or the peripheral interface 15, the logic control unit 12 receives the target command, transmits the control signal to the RF generation module 13, and meanwhile transmits the control signal to the relay, so that the switch circuit is at a target position to form a closed loop with the circuit in the handle and the catheter tip. Through the appropriate arrangement of the RF generation module and the handle, it is able to share one RF generation module 13 in the three operating modes.

In a possible embodiment of the present disclosure, the switch circuit includes a first switch circuit, a first selection end (RF_positive1) of which is electrically coupled to the first region of the RF catheter to form the first loop, a second selection end (RF_positive2) of which is electrically coupled to the second region of the RF catheter to form the second loop, and a third selection end (RF_positive3) of which is electrically coupled to the third region of the RF catheter to form the third loop.

In the embodiments of the present disclosure, through different circuit arrangement modes on a Printed Circuit Board Assembly (PCBA) in the handle, it is able for the first heating coil to be connected in series to, or in parallel to, the second heating coil.

As shown in FIG. 8, the heating coils are connected in series to each other on the PCBA in the handle, outputs of the RF generation module 13 are defined as RF_output+ and RF_output−, and inputs in the first mode are defined as RF_positive1 and RF_negative. The RF is outputted through RF+ after passing through RF_output+, RF_positive1 and the PCBA in the handle, and then flows back to the RF generation module 13 through RF_output− after passing through the human body, RF−, the PCBA in the handle and RF_negative.

In the second mode, inputs are defined as RF_positive2 and RF_negative. The RF is outputted through RF_negative after passing through RF_output+, RF_positive2, the PCBA in the handle, the second heating coil and the first heating coil.

In the third mode, inputs are defined as RF_positive3 and RF_negative, and the RF is outputted through RF_negative after passing through RF_output+, RF_positive3, the PCBA in the handle and the first heating coil.

As shown in FIG. 9, in another possible embodiment of the present disclosure, the switch circuit includes a second switch circuit, the second switch circuit includes a first-stage switch circuit and a second-stage switch circuit, a first selection end (RF_positive1) of the first-stage switch circuit is electrically coupled to the first region of the RF catheter to form the first loop, a second selection end of the first-stage switch circuit is electrically coupled to a first selection end (RF_positive2) of the second-stage switch circuit and the second region of the RF catheter to form the second loop, and a third selection end of the first-stage switch circuit is electrically coupled to a second selection end (RF_positive3) of the second-stage switch circuit and the third region of the RF catheter to form the third loop.

In the embodiments of the present disclosure, the first heating coil is connected in parallel to the second heating coil through the arrangement of second-stage switch circuit and the circuits on the PCBA in the handle. When RF_output+ is electrically coupled to RF_positive2, the second-stage switch circuit is switched on, i.e., RF_positive2 is electrically coupled to RF_positive3. At this time, the RF catheter operates in the second mode. After the RF is inputted through RF_output+, in a first branch, the RF is outputted through RF_output− after passing through the second heating coil and RF_negative, and in a second branch, the RF is outputted through RF_output− after passing through RF_positive2, RF_positive3, the first heating coil and RF_negative.

When RF_output+ is electrically coupled to RF_positive3 and the second-stage switch circuit is switched off, the RF catheter operates in the third mode. The RF is inputted through RF_output+, and outputted through RF_output− after passing through the first heating coil and RF_negative.

In the embodiments of the present disclosure, the catheter is delivered to the position where the lesion of the blood vessel occurs through a guide wire and a sheath, so that the annular electrode is located in the perforating vein and the plurality of heating coils is located in the superficial vein.

Merely a region A is triggered through a button on the handle, a screen of an RF energy generator or a foot switch, so as to start the ablation on the perforating vein.

Merely a region B is triggered through the button on the handle, the screen of the RF energy generator or the foot switch, so as to start the ablation on the superficial vein surrounding the region B. Through selecting the region B, it is able to improve the ablation efficiency of the catheter.

The catheter is withdrawn by a certain distance in accordance with the marking tape, so as to complete the treatment on the other segments of superficial vein in a same way as that mentioned hereinabove.

When a length of the to-be-treated segment of the superficial vein is smaller than a total length of the heating coils, it is necessary to continuously adjust the gear position, and merely trigger a region C, thereby to treat the remaining segments of the short vein.

The catheter is withdrawn from the body of the patient, and a puncture point is subjected to bandaging and hemostasis, so as to complete the operation.

According to the embodiments of the present disclosure, it is able to complete the RF closure on the superficial vein and the perforating vein of the lower limb simultaneously while ensuring the high ablation efficiency. The catheter is provided with a single electrode or two electrodes at the distal end for the RF treatment on the perforating vein. The catheter includes the plurality of heating coils for the treatment on the superficial vein. Each heating coil is controlled independently and outputs the energy independently, so the heating coil may be selected dynamically in use. Through the plurality of heating coils, it is able to perform the ablation on a long vein segment and a short vein segment through a single catheter, without any attenuated ablation efficiency. According to the catheter in the embodiments of the present disclosure, it is able to not only perform the RF ablation through bipolar or unipolar RF, but also perform the RF ablation through heat conduction. In addition, it is able to achieve the rapid exchange or over-the-wire (OTW) exchange of the catheter, thereby to facilitate the accurate intervention of the catheter to the position where the lesion of the blood vessel occurs.

As shown in FIG. 10, the present disclosure further provides in some embodiments an RF catheter controlling method, which includes: Step 11 of receiving a target command, the target command being used to indicate a target mode of an RF catheter; Step 12 of generating a control signal in accordance with the target command, the control signal carrying information about at least one RF parameter corresponding to the target mode; and Step 13 of controlling the RF catheter to operate in the target mode in accordance with the information about the at least one RF parameter.

In a possible embodiment of the present disclosure, the method further includes: Step 13 of receiving an RF start command or an RF stop command; and Step 14 of starting an output of an RF signal in accordance with the RF start command in the target mode or stopping the output of the RF signal in accordance with the RF stop command in the target mode.

In the embodiments of the present disclosure, the method will be described hereinafter in more details.

1. The command is transmitted to the logic control unit 12 through the GUI or the other Input/Output (IO) interface, so as to determine the operating mode of the energy output segment at a distal end of the RF catheter.

2. After the operating mode has been determined, the logic control unit 12 sets parameters for the RF generation module 13 in accordance with a core algorithm, and transmits a signal to the RF generation module 13 for outputting the RF energy.

3. The RF generation module 13 starts an energy generation mechanism in accordance with the parameters, and transmits the RF energy through an interface to the energy output segment. Due to a feedback signal, the RF generation module 13 may be in a constant power output mode or a constant temperature output mode.

4. The energy output segment at the distal end of the RF catheter applies, directly or indirectly, the energy to the target tissue in the blood vessel for treatment.

5. When the energy is outputted by the RF generation module 13, the logic control unit 12 may stop the energy output under a target circumstance.

6. After the treatment at a first stage has been completed, the position of the RF catheter in the blood vessel is adjusted, and the RF catheter is switched to the other operating mode through the GUI or the other IO interface for the treatment at a second stage.

7. The energy output in a specific operating mode may be repeated at a certain stage according to the therapeutic demand.

According to the embodiments of the present disclosure, through the system, it is able to select the operating mode of the RF catheter, and complete the treatment in different operating modes through one RF energy generator, thereby to reduce the operation complexity and improve the convenience. In other words, it is able to complete the RF closure on the superficial vein and the perforating vein of the lower limb simultaneously through one RF catheter while ensuring the ablation efficiency of the RF catheter.

It should be appreciated that, the implementation of the method may refer to that of the system with a same technical effect.

It should be appreciated that, units and steps described in the embodiments of the present disclosure may be implemented in the form of electronic hardware, or a combination of a computer program and the electronic hardware. Whether or not these functions are executed by hardware or software depends on specific applications or design constraints of the technical solution. Different methods may be adopted with respect to the specific applications so as to achieve the described functions, without departing from the scope of the present disclosure.

It should be further appreciated that, for convenience and clarification, operation procedures of the system, device and units described hereinabove may refer to the corresponding procedures in the method embodiment, and thus will not be particularly defined herein.

It should be further appreciated that, the device and method may be implemented in any other ways. For example, the embodiments for the apparatus is merely for illustrative purposes, and the modules or units are provided merely on the basis of their logic functions. During the actual application, some modules or units may be combined together or integrated into another system. Alternatively, some functions of the module or units may be omitted or not executed. In addition, the coupling connection, direct coupling connection or communication connection between the modules or units may be implemented via interfaces, and the indirect coupling connection or communication connection between the modules or units may be implemented in an electrical or mechanical form or in any other form.

The units may be, or may not be, physically separated from each other. The units for displaying may be, or may not be, physical units, i.e., they may be arranged at an identical position, or distributed on a plurality of network elements. Parts or all of the units may be selected in accordance with the practical need, so as to achieve the purpose of the present disclosure.

In addition, the functional units in the embodiments of the present disclosure may be integrated into a processing unit, or the functional units may exist independently, or two or more functional units may be combined together.

In the case that the functional units are implemented in a software form and sold or used as a separate product, they may be stored in a computer-readable medium. Based on this, the technical solutions of the present disclosure, partial or full, or parts of the technical solutions of the present disclosure contributing to the related art, may appear in the form of software products, which may be stored in a storage medium and include several instructions so as to enable computer equipment (a personal computer, a server or network equipment) to execute all or parts of the steps of the method according to the embodiments of the present disclosure. The storage medium includes any medium capable of storing therein program codes, e.g., a universal serial bus (USB) flash disk, a mobile hard disk (HD), a read-only memory (ROM), a random access memory (RAM), a magnetic disk or an optical disk.

It should be further appreciated that, according to the device and the method in the embodiments of the present disclosure, the members and/or steps may be subdivided and/or recombined, which shall also be deemed as equivalents of the present disclosure. In addition, the steps for executing the above-mentioned processings may be performed in a chronological order. Of course, some steps may also be performed in parallel, or independently of each other. It should be further appreciated that, after reading the descriptions of the present disclosure, it is able for a person skilled in the art, using a basic programming skill, to implement any or all steps of the method and any or all members of the device in any computing device (including a processor and a storage medium) or a network consisting of the computing devices, in the form of hardware, firmware, software or a combination thereof.

Hence, the purposes of the present disclosure may also be implemented by one program or a set of programs running on any computing device, e.g., a known general-purpose computer, or implemented merely by a program product including programs codes capable of implementing the method or device. In other words, this program product and a storage medium storing therein the program product also constitute a part of the present disclosure. Obviously, the storage medium may be any known storage medium or a storage medium that may occur in future. It should be further appreciated that, according to the device and the method in the embodiments of the present disclosure, the members and/or steps may be subdivided and/or recombined, which shall also be deemed as equivalents of the present disclosure. In addition, the steps for executing the above-mentioned processings may be performed in a chronological order. Of course, some steps may also be performed in parallel, or independent of each other.

The above embodiments are for illustrative purposes only, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A Radio Frequency (RF) catheter controlling system, comprising:

a logic control unit configured to receive a target command, and generate a control signal in accordance with the target command, the target command being used to indicate a target mode of an RF catheter, the control signal carrying information about at least one RF parameter corresponding to the target mode; and an RF generation module in communication with the logic control unit and configured to control the RF catheter to operate in the target mode in accordance with the information about the at least one RF parameter corresponding to the target mode, wherein the target mode is one of a first mode, a second mode and a third mode;

in the first mode, a first region of an RF energy output segment of the RF catheter operates, and the first region comprises a first electrode and a second electrode spaced apart from each other;

in the second mode, a second region of the RF energy output segment of the RF catheter operates, and the second region comprises a first heating coil and a second heating coil spaced apart from each other;

in the third mode, a third region of the RF energy output segment of the RF catheter operates, and the third region comprises the first heating coil; and the first heating coil is arranged adjacent to the second electrode, and wherein the RF generation module is configured to:

in the first mode, generate a target RF signal in accordance with a first control signal, the first control signal carrying a first frequency parameter, a first power parameter, a first temperature parameter, a first load parameter, a first impedance parameter, a first output power parameter and a first treatment time parameter;

in the second mode, generate the target RF signal in accordance with a second control signal, the second control signal carrying a second frequency parameter, a second power parameter, a second temperature parameter, a second load parameter, a second impedance parameter, a second output power parameter and a second treatment time parameter; and in the third mode, generate the RF frequency signal in accordance with a third control signal, the third control signal carrying a third frequency parameter, a third power parameter, a third temperature parameter, a third load parameter, a third impedance parameter, a third output power parameter and a third treatment time parameter, wherein the first load parameter is a human tissue, the second load parameter is the first heating coil and the second heating coil, and the third load parameter is the first heating coil.

2. The RF catheter controlling system according to claim 1, further comprising an upper computer and/or a peripheral interface in communication with the logic control unit, wherein the logic control unit receives the target command from the upper computer and/or the peripheral interface, and the target command is generated when a button on an operation interface of the upper computer is pressed and/or inputted through a physical switch coupled to the peripheral interface.

3. The RF catheter controlling system according to claim 1, wherein the RF generation module is further configured to receive an RF start command or an RF stop command, and start an output of an RF signal in accordance with the RF start command in the target mode, or stop the output of the RF signal in accordance with the RF stop command in the target mode.

4. The RF catheter controlling system according to claim 1, wherein the RF generation module further comprises:

an RF signal generation unit configured to generate an RF signal;

an RF positive pole configured to transmit the RF signal;

an RF negative pole configured to receive an RF signal from an energy applying end of the RF catheter; and a switch circuit coupled to the RF positive pole, and configured to be electrically coupled to the first region of the RF catheter in the first mode to form a first loop, electrically coupled to the second region of the RF catheter in the second mode to form a second loop, and electrically coupled to the third region of the RF catheter in the third mode to form a third loop.

5. The RF catheter controlling system according to claim 4, wherein the switch circuit comprises a first switch circuit, a first selection end of which is electrically coupled to the first region of the RF catheter to form the first loop, a second selection end of which is electrically coupled to the second region of the RF catheter to form the second loop, and a third selection end of which is electrically coupled to the third region of the RF catheter to form the third loop.

6. The RF catheter controlling system according to claim 4, wherein the switch circuit comprises a second switch circuit, the second switch circuit comprises a first-stage switch circuit and a second-stage switch circuit, a first selection end of the first-stage switch circuit is electrically coupled to the first region of the RF catheter to form the first loop, a second selection end of the first-stage switch circuit is electrically coupled to a first selection end of the second-stage switch circuit and the second region of the RF catheter to form the second loop, and a third selection end of the first-stage switch circuit is electrically coupled to a second selection end of the second-stage switch circuit and the third region of the RF catheter to form the third loop.

7. An RF catheter controlling method for an RF catheter controlling system comprising an RF catheter, comprising:

receiving a target command, the target command being used to indicate a target mode of the RF catheter;

generating a control signal in accordance with the target command, the control signal carrying information about at least one RF parameter corresponding to the target mode; and controlling the RF catheter to operate in the target mode in accordance with the information about the at least one RF parameter, wherein the target mode is one of a first mode, a second mode and a third mode;

in the first mode, a first region of an RF energy output segment of the RF catheter operates, and the first region comprises a first electrode and a second electrode spaced apart from each other;

in the second mode, a second region of the RF energy output segment of the RF catheter operates, and the second region comprises a first heating coil and a second heating coil spaced apart from each other;

in the third mode, a third region of the RF energy output segment of the RF catheter operates, and the third region comprises the first heating coil; and the first heating coil is arranged adjacent to the second electrode, and wherein the control signal comprises a first control signal for the first mode, a second control signal for the second mode, and a third control signal for the third mode, the first control signal carrying a first frequency parameter, a first power parameter, a first temperature parameter, a first load parameter, a first impedance parameter, a first output power parameter and a first treatment time parameter;

the second control signal carrying a second frequency parameter, a second power parameter, a second temperature parameter, a second load parameter, a second impedance parameter, a second output power parameter and a second treatment time parameter; and the third control signal carrying a third frequency parameter, a third power parameter, a third temperature parameter, a third load parameter, a third impedance parameter, a third output power parameter and a third treatment time parameter, wherein the first load parameter is a human tissue, the second load parameter is the first heating coil and the second heating coil, and the third load parameter is the first heating coil.

8. The RF catheter controlling method according to claim 7, further comprising:

receiving an RF start command or an RF stop command; and starting an output of an RF signal in accordance with the RF start command in the target mode or stopping the output of the RF signal in accordance with the RF stop command in the target mode.

* * * * *